United States Patent [19]
Dolnik et al.

[11] Patent Number: 6,074,542
[45] Date of Patent: Jun. 13, 2000

[54] COMPOUNDS FOR MOLECULAR SEPARATIONS

[76] Inventors: Vladislav Dolnik, 575 S. Rengstorff Ave. #90, Mountain View, Calif. 94040; Marcella Chiari, V. Gian Battista Brocchi, 11, Milano, Italy, 20131

[21] Appl. No.: 09/324,892

[22] Filed: Jun. 3, 1999

Related U.S. Application Data

[62] Division of application No. 09/016,465, Jan. 30, 1998, abandoned.

[51] Int. Cl.$^7$ .......................... G01N 27/26; G01N 27/447
[52] U.S. Cl. .......................... 204/454; 204/451; 204/455; 204/601; 204/655
[58] Field of Search .................................... 204/451, 452, 204/453, 454, 455, 601, 602, 603, 604, 605

[56] References Cited

U.S. PATENT DOCUMENTS

| | | | |
|---|---|---|---|
| 5,089,111 | 2/1992 | Zhu et al. ................................ | 204/451 |
| 5,143,753 | 9/1992 | Novotny et al. ......................... | 427/299 |
| 5,470,916 | 11/1995 | Righetti et al. .......................... | 525/296 |
| 5,567,292 | 10/1996 | Madabhushi et al. ................... | 204/451 |

OTHER PUBLICATIONS

S. Hjerten, "High Performance Electrophoresis: Elimination of Electro–endosmosis and Solute Adsorption" Journal of Chromatography vol. 347 (1985) 191–198, no month available.

N. Iki and E. Yeung, "Non–bonded poly(ethylene oxide) polymer–coated column for protein separation by capillary electrophoresis", *Journal of Chromatography* A, 731 No month available (1996), pp. 273–282.

M. Huang et al., "Hydrolytically stable cellulose–derivative coatings for capillary electrophoresis of peptides, proteins and glycoconjugates", *Electrophoresis* 16 No month available (1995), pp. 396–401.

A. Cifuentes et al., "Selectivity change in the separation of porteins and peptides by capillary electrophoresis using high–molecular–mass polyethyleneimide", *Journal of Chromatography* B, 681 No month available (1996), pp. 21–27.

S. Hjerten, "High–Performance electrophoresis; Elimination of of electroendosmosis and Solute Adsorption", *Journal of Chromagraphy*, 347 No month available (1985), pp. 191–198.

M. Huang et al., "Evaluation of Surface–bonded Polyethylene Glycol and Polyethylene Imine in Capillary Electrophoresis", *J. Microcol.* Sep. 4 (1992), pp. 135–143.

M. Chiari et al., "Capillary electrophoretic separation of proteins using stable, hydrophilic poly(acryloylaminoethoxyethanol)–coated columns", *Journal of Chromatography* A, 717 No month available (1995), pp. 1–13.

M. Chiari et al., "Synthesis and Characterization of Capillary Columns Coated with Glycoside–Bearing Polymer", *Analytical Cheminstry*, vol. 68, No. 17, Sep. 1, 1996, pp. 2731–2736.

E. Simo-Alfonso et al., "Novel acrylamido monomers with higher hydrophilicity and improved hydrolytic stability: I. Synthetic route and product characterization", *Electrophoresis* 17, No month available 1996.

S. Hjerten, "A new type of pH– and detergent–stable coating for elimination of electroendosmosis and adsorption in (capillary) electrophoresis", *Electrophoresis* 14, No month available 1993, pp. 390–395.

*Primary Examiner*—Jill Warden
*Assistant Examiner*—John S. Starsiak
*Attorney, Agent, or Firm*—Thomas Schneck; David M. Schneck

[57] ABSTRACT

The present invention describes a method and apparatus utilizing a capillary coating of linear and crosslinked polymers and copolymers of acrylamidomonomers or methacrylamides bearing two hydroxyethyl residues. The method and apparatus employ this coating to maintain coating integrity and suppress electroosmotic flow under basic conditions in capillary electrophoresis.

14 Claims, 5 Drawing Sheets

COMPOUNDS FOR MOLECULAR SEPARATIONS

CROSS-REFERENCE TO RELATED APPLICATION

This is a divisional application of U.S. Ser. No. 09/016,465 filed Jan. 30, 1998 now abandoned.

TECHNICAL FIELD

The present invention generally relates to compounds for chromatography and electrophoresis. Specifically, the invention is directed to the use of capillary coatings to reduce electroosmotic flow.

BACKGROUND ART

Capillary electrophoresis has achieved a remarkably rapid development from its introduction in the early 1980s. This technique miniaturizes the electrophoretic process and presents remarkable advantages over traditional slab gel electrophoretic techniques. The most significant limitation in slab gel electrophoresis is the Joule heating which results from current flow through the system. When the electrophoretic process is carried out in a capillary with an internal diameter of 25–100 μm, the Joule heat is dissipated from the surface more efficiently than from any other support, allowing the use of higher voltage and increasing separation efficiency and velocity.

Separation efficiency of columns in capillary electrophoresis can be expressed as a number of theoretical plates generated per a unit length of column for a standard substance. The equation relating number of theoretical plates N to mobility of analyte μ, voltage V, and diffusion coefficient D is:

$$N=\mu V/2D.$$

This equation takes into account only diffusion as a factor influencing separation efficiency. Nevertheless, there are other effects which influence separation efficiency: electromigration dispersion, produced Joule heat, the length of the sampling plug, sorptions on the capillary wall, length of detection cell, and eddy migration. Sorption and eddy migration are directly affected by the quality of the inner capillary surface. A fused silica capillary has approximately 5 silanol groups per square nanometer. Silanol groups behave as a weak acid, ionizing in water with a broad titration curve from pH 2 to 9. Silanols' dissociation generates charges as an integral part of the wall. If an analyte interacts with the capillary wall, typically by Coulombic interactions, the migration of molecules close to the capillary wall is decelerated and the analyte peak is tailing.

Distribution of macromolecules between the buffer and the wall causes bandspreading and poor reproducibility of transit times. Reversible interactions between analytes and a capillary surface worsen the separation profile, broadening the peaks and decreasing reproducibility, while irreversible interactions completely destroy the profile.

Presence of a negative charge on the capillary surface is a source of electroosmotic flow: the negatively charged surface is supposed to migrate in the electric field; because the charged groups are immobilized on the capillary surface, it is the liquid inside the capillary which moves, generating so-called electroosmotic flow. In some respect the presence of electroosmotic flow can be advantageous, since it allows analytes with very low mobilities to get through the detector (e.g., gamma globulins of serum proteins, or simultaneous analysis of cations and anions as frequently needed in the case of peptide mapping). The electroosmotic flow profile is typically of a plug-shape and does not deteriorate separation significantly. However, if the surface charge at the capillary surface is not homogenous, an electroosmotic flow of different velocity generates lengthwise along the capillary which generates eddy migration (see FIG. 1). Eddy migration causes significant peak broadening and loss of separation efficiency. Therefore, to achieve high separation efficiencies, the electroosmotic flow has to be equalized. However, if there is a residual charge on the capillary surface, this allows sorption on the wall and thus locally reduces the electroosmotic flow. Generated inhomogeneities cause eddy migration. Because of that, electroosmotic flow needs to be eliminated completely to achieve the highest separation efficiency.

There are typically two approaches to the elimination of the electroosmotic flow. In the first approach, a dynamic coating is formed. This can be effected by addition of a polymer or a surfactant to the background electrolyte (BGE) or is made by adding suitable cations (polycations, cationic detergents, multicharged cations). The neutral polymer interacts with the capillary wall and shields it from the liquid. Simultaneously, it increases viscosity in the electric double layer and thus reduces electroosmotic flow. Various cellulose derivatives and other hydrophilic polymers have been used for years for this purpose. Examples of this technique include use of polyethyleneoxide, described by Iki and Yeung (J. Chromatogr. A 731, 1996, 273–282) and the use of a copolymer of hydroxypropylcellulose and hydroxyethyl-methacrylate described by Huang, et al. (Electrophoresis 16, 1995, 396–401).

Cationic additives titrate the negative charge of the capillary wall so that the electrokinetic potential and electroosmotic flow are decreased, neutralized or even reversed. In some cases the capillary is flushed with a solution of the cation prior to filling with BGE instead of adding the cation to BGE. Polycations and cationic surfactants have been used recently to coat the capillary wall dynamically, as described by Cifuentes, et al. (J. Chromatography B 681, 1996, 21–27).

Better results are obtained if a permanent (or static) wall coating is formed. Permanent wall coatings for capillary electrophoresis usually consists of two layers. An early permanent coating was described by Hjerten in J. Chromatography 347, 1985, 191–198. Hjerten describes attaching bifunctional 3-methacryloxypropyltrimethoxysilane to the capillary wall in the presence of linear polyacrylamide. In this way, electroosmosis and sorptions were eliminated. However, 3-methacryloxypropyltrimethoxysilane is attached to the capillary wall via siloxane bonding which is hydrolytically unstable at alkali pH. That is why a capillary coated with this film is stable at pH≦7 only. Given that many electrophoretic protocols require alkali pH, an alkali stable coating is needed.

Novotny et al. (U.S. Pat. No. 5,143,753) describe a protective coating from polyacrylamide, using vinylmagnesium bromide to attach the polymer to the capillary wall. In the beginning of the procedure, the fused silica surface is activated by reaction with thionyl chloride and the vinyl group is connected by the reaction with vinylmagnesium bromide. The formed coating is attached to the capillary wall via Si—C bond and not via siloxane bond; therefore, a significantly better stability of the coating is achieved at alkali pH. The capillary is free of any electroosmotic flow and the coating is stable at pH=9.5 for approximately 7 days; after that the migration times get longer, which is a result of increasing electroosmotic flow. This is a consequence of hydrolysis of amide groups in polyacrylamide and an increasing electrokinetic potential on the capillary wall. The polymer shields the residual silanol groups and simultaneously increases viscosity in the electric double layer.

Besides γ-methacryloxypropyltrimethoxysilane and Grignard chemistry, bifunctional reagents have also been used to attach a polymer layer to the capillary wall. Examples include Huang, et al. (J. Microcol. Sep. 4, 1992, 135–143) using bifunctional crosslinked siloxane, and chiari, et al. (J. Chromatogr. A 717, 1995, 1–13) using catalytical hydrosilylation followed by reaction with allylmethacrylate.

Polyacrylamide is the most frequently used polymer for wall coating. However, its hydrolytic instability limits the life time of the prepared wall coating. Crosslinking polyacrylamide is one way to increase the stability of the coating. Another way to increase the stability of the wall coating is either to replace acrylamide with a more stable monomer, such as acryloylaminoethoxyethanol as described by Chiari, et al. (J. Chromatogr. A 717, 1995, 1–13; see also Righetti & Chiari, U.S. Pat. No. 5,470,916), acryloylaminoethoxyethylglucose as described by Chiari et al. (Anal Chem 68, 1996, 2731–2736), or acryloylaminopropanol as described by Simo-Alfonso, et al., Electrophoresis 17, 1996, 723–731), or to use a chemically activated stable polymer, such as hydroxymethylcellulose or dextran as described by Hjerten and Kubo (Electrophoresis 14, 1993, 390–395). Acryloylaminoethoxyethylglucose provides a hydrolytically very stable coating which, at pH 8.5, supports without an obvious electroosmotic flow and a loss of resolution at least 300 runs for separation of proteins.

As the above shows, there are many possibilities to limit electroendoosmosis in capillary tubes. However each has limitations.

It is the initial object of the invention to describe a novel compound for minimizing the effects of electroosmosis and a method to produce this compound. The monomers of this compound must be able to be polymerised into a stable polymer.

It is another object of the invention to produce a coating for the interior of capillary tubes that reduces electrooosmosis.

It is a further goal to produce a coating that is stable at a wide pH range including alkaline pH levels.

It is a further goal to produce a coating that is stable for hundreds of electrophoretic runs. Once a capillary coating degrades, it has to be replaced. This produces material costs. Any coating that allows additional electrophoretic runs without degradation would help minimize these costs.

SUMMARY OF THE INVENTION

The present invention is a compound having the formula:

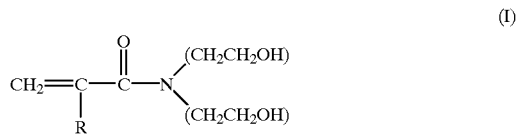

(I)

where R is H— or $CH_3$—. The present invention is also a method of producing this compound by combining diethanol amine, cooled to −50° C., with acryloylchloride or methacryloylchloride. The monomers of formula (I) can be polymerized to form linear and crosslinked polymers. The monomers of formula (I) can be used to form a polymer either alone as a homopolymer or as a copolymer with acrylamide or other monomers.

The present invention is useful as a capillary coating that satisfies the above objectives. The coating described eliminates electroosmotic flow and reduces adsorption on the capillary surface. The coating, as seen in the FIGS. , is stable even after numerous electrophoretic runs under basic conditions.

Specifically, the coating of the present invention is a polymer of the formula (I) in which R is either —H or —$CH_3$. This chemical can be used either as a homopolymer, or as a copolymer with other monomers such as acrylamide.

The present invention is also a method of preparing the above coating and using this coating to cover the interior of a capillary tube. This process involves introducing a mixture of above formula (I) monomer into the pre-treated capillary and a catalytic inducer into a capillary tube section. The mixture would then polymerize, forming a coating on the interior capillary wall.

During the process of coating the interior capillary, compound of formula (I) can be used alone as a homopolymer or as a copolymer with another monomer. Again, acrylamide is one possible monomer.

capillary: 75 μm I.D., 196 μm O.D., total length 75 cm, effective length 40 cm, the wall coating made by polymerization of acryloyldiethanolamine; detection: laser-induced fluorescence (argon-ion laser, 488 nm) at 530 nm. The electropherogram shows DNA sequencing run # 500 in five randomly selected capillaries.

Figure 4:
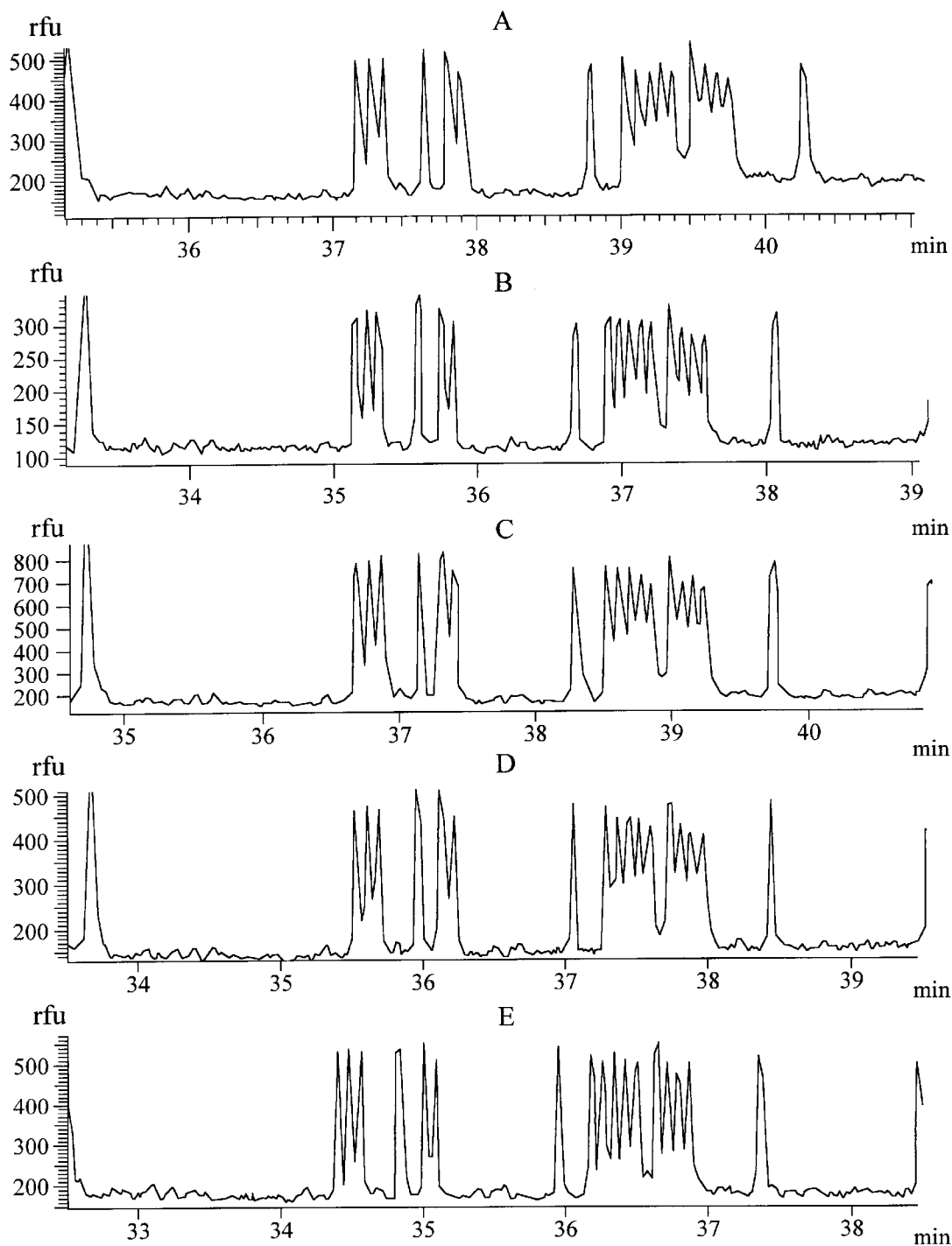
FIGS. 4A–4E shows part of an electropherogram of M13mp18, T-track with a peak quintuplet and quadruplet. Separation conditions: background electrolyte: 79 mM boric acid, 79 mM Tris, 1 mM EDTA, 6 N urea, 10% formamide, 2% hydroxyethylcellulose (MW: 90–105 k); voltage: 12 kV.

FIGS. 5A–5F shows part of an electropherogram of DNA sequencing run #118 when wall coating made from acrylamide is used in 6 randomly selected capillaries under the same conditions described in FIG. 4.

BEST MODE FOR CARRYING OUT THE INVENTION

The compound of the formula (I) is prepared according to the present invention by direct reaction of acryloylchloride or methacryloylchloride with diethanolamine. Because of the presence of hydroxyl groups which can react with the acryloylchloride or methacryloylchloride, the reaction is preferably performed at low temperature about −50° C.

The attachment of the polymer of the compound of formula (I) or a copolymer made of compound (I) and other monomer, e.g., acryloylaminoethoxyethylglucopyranose (AEG), to the capillary wall bearing unsaturated moieties is performed by polymerization of acryloyldiethanolamine or methacryloyldiethanolamine inside the capillary. To get a homogenous wall coating in long capillary sections, the polymerizing mixture does not contain catalyst such as TEMED or triethanolamine, it contains the compound of formula (I) and an initiator. Examples of polymerization initiators are free radical initiators such as peroxides, persulfates or azo compounds. Examples are benzoyl chloride, tert-butyl peroxide, azobiscyanovaleric acid, azobiscyclohexane-carbonitrile and persulfates such as potassium persulfate and ammonium persulfate. The capillary is filled with the polymerizing mixture at room or decreased temperatures and only after it is filled, it is heated to accelerate the polymerization.

EXAMPLE 1
Synthesis of acryloyldiethanolamine (ADEA)

A mixture of 500 ml of absolute alcohol, 1.0 mol (101 g) triethylamine, 0.2 g p-methoxyphenol, and 1.0 mol (159 g) diethanolamine was dried over a molecular sieve (All molecular sieves should work.) and filtered through 0.45 μm membrane filter into a three-neck flask with additional funnel, thermometer and nitrogen inlets. The flask was cooled to −50° C. by immersing in dry ice/alcohol bath while under nitrogen atmosphere. 1.0 mol of acryloylchloride was added slowly to keep temperature above −48° C. One hour after adding all acryloyl chloride the temperature was allowed to increase to −20° C., triethylamine-HCl was precipitated and removed by filtration. The filtrate was pooled with 100 ml −20° C. ethanol and was passed through Amberlite IRA-900 column.

EXAMPLE 2
Alkaline hydrolysis of free ADEA monomers

Figure 1:
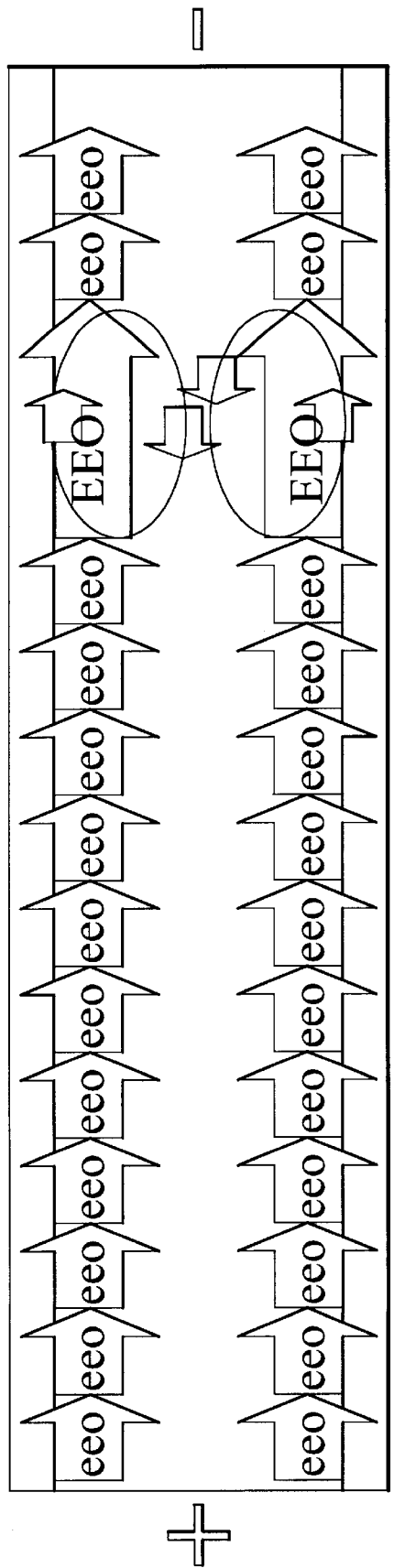
FIG. 1 is a schematic depicting the effect that eddy migration (resulting from uneven coating) has on the flow within a capillary.
Figure 2:
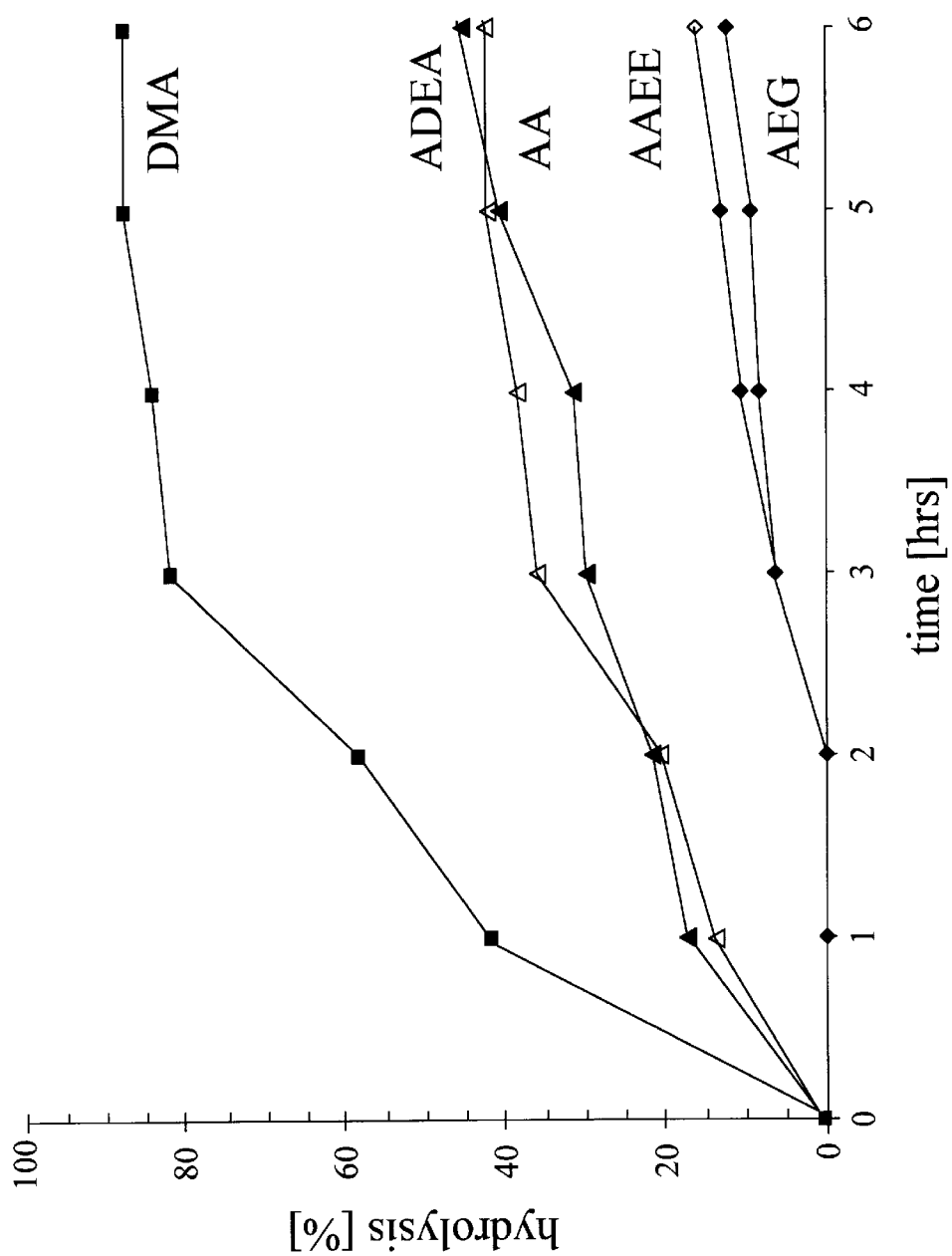
FIG. 2 represents the kinetics of hydrolysis of different monomers in free solution. Conditions: 0.1N NaOH, 70° C., for 1–6 h. The percentage of undegraded monomer was estimated by CZE. Abbreviations: ADEA, acryloyldiethanolamine; AA, acrylamide; DMA, dimethylacrylamide; AAEE, N-acryloylaminoethylethanol; AEG, N-(acryloylaminoethoxy)ethyl-β-D-glycopyranoside.
Figure 3:
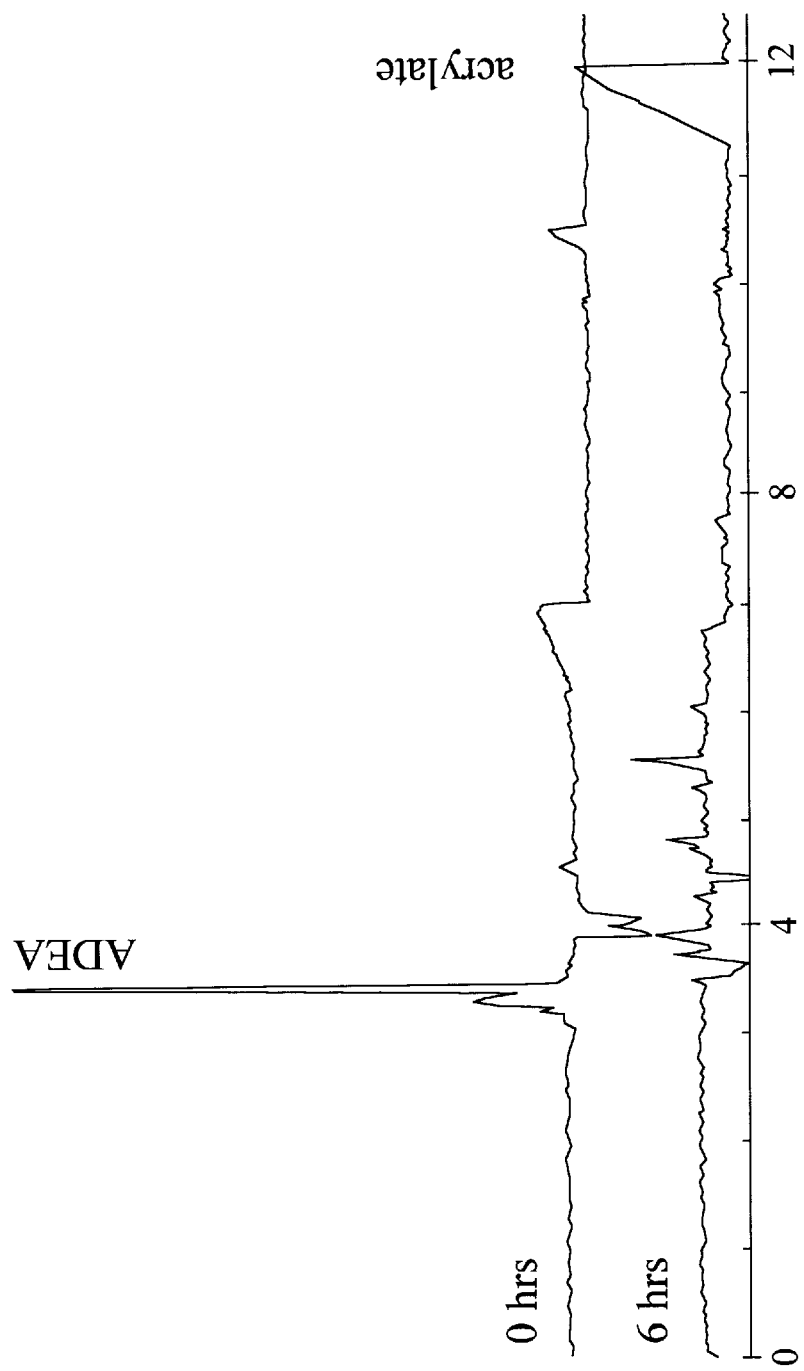
FIG. 3 shows an electropherogram of acryloyldiethanolamine after 0 and 6 hours of hydrolysis at 70° C. in 0.1 M NaOH. Separation conditions: background electrolyte: 100 mM SDS, 20 mM Tris, 20 mM Tricine; voltage: 15 kV; capillary: 75 μm I.D., 196 μm O.D., total. length 50 cm, effective length 40 cm; detection: UV absorption at 190 nm.

A 30 mM solution of ADEA monomer in 0.1 NaOH was incubated at 70° C. for 6 hours. At given time intervals, aliquots were collected and analyzed by micellar electrokinetic chromatography in an uncoated capillary 75 μm I.D. 195 μm O.D., total length 50 cm, effective length 40 cm, with background electrolyte: 100 mM SDS, 20 mM Tris, 20 mM Tricine applying voltage of 15 kV, detecting the zone by measuring UV absorptionn at 190 nm. The peak areas, extrapolated to an equal migration velocity, have been used to calculate the degree of hydrolysis. FIG. 3 shows the electropherogram of ADEA after 0 and 6 hours of hydrolysis.

EXAMPLE 3
Preparation of the wall coating

A 100-m length of fused silica capillary (75 μm I.D. 195 μm O.D.) was placed in 70° C. water bath and flushed with thionyl chloride from a chamber pressurized with dry nitrogen to 13.8 Mpa (2000 psi). After 100 μl of thionylchloride passed through the distal end of the capillary, the pressure was reduced to 1.4 Mpa (200 psi) and the capillary was flushed with thionylchloride for at least 12 hours. When approximately 1 ml total of thionylchloride had passed through the capillary, a 2.5 ml gastight Hamilton syringe was filled with 1 M vinyl-magnesium bromide and attached to the capillary inside the pressure chamber. The chamber was then pressurized to 13.8 Mpa (2000 psi). The capillary was voided of thionyl chloride and when vinylmagnesium bromide appeared at the capillary end, the pressure was reduced to 1.4 Mpa (200 psi). The flushing with vinylmagnesium bromide continued for 6 hours. The syringe was then replaced with another one filled with anhydrous tetrahydrofurane. The capillary was rinsed with 2.5 ml tetrahydrofurane at 13.8 mPa followed with 3 ml of deionized water and with nitrogen. At room temperature the capillary is filled with a fresh mixture containing 5% acryloyldiethanolamine and 0.5% azobiscyanovaleric acid. In an alternative embodiment, the acryloyldiethanolamine is mixed with another suitable monomer. This monomer could be AEG, AAEE, or acrylamide depending on the experimental protocol. After the capillary is completely filled, it was placed in 70° C. water bath for 30±0.5 min. Then it was cooled down to room temperature and flushed with at least 5 ml of deionized water.

Figure 5:
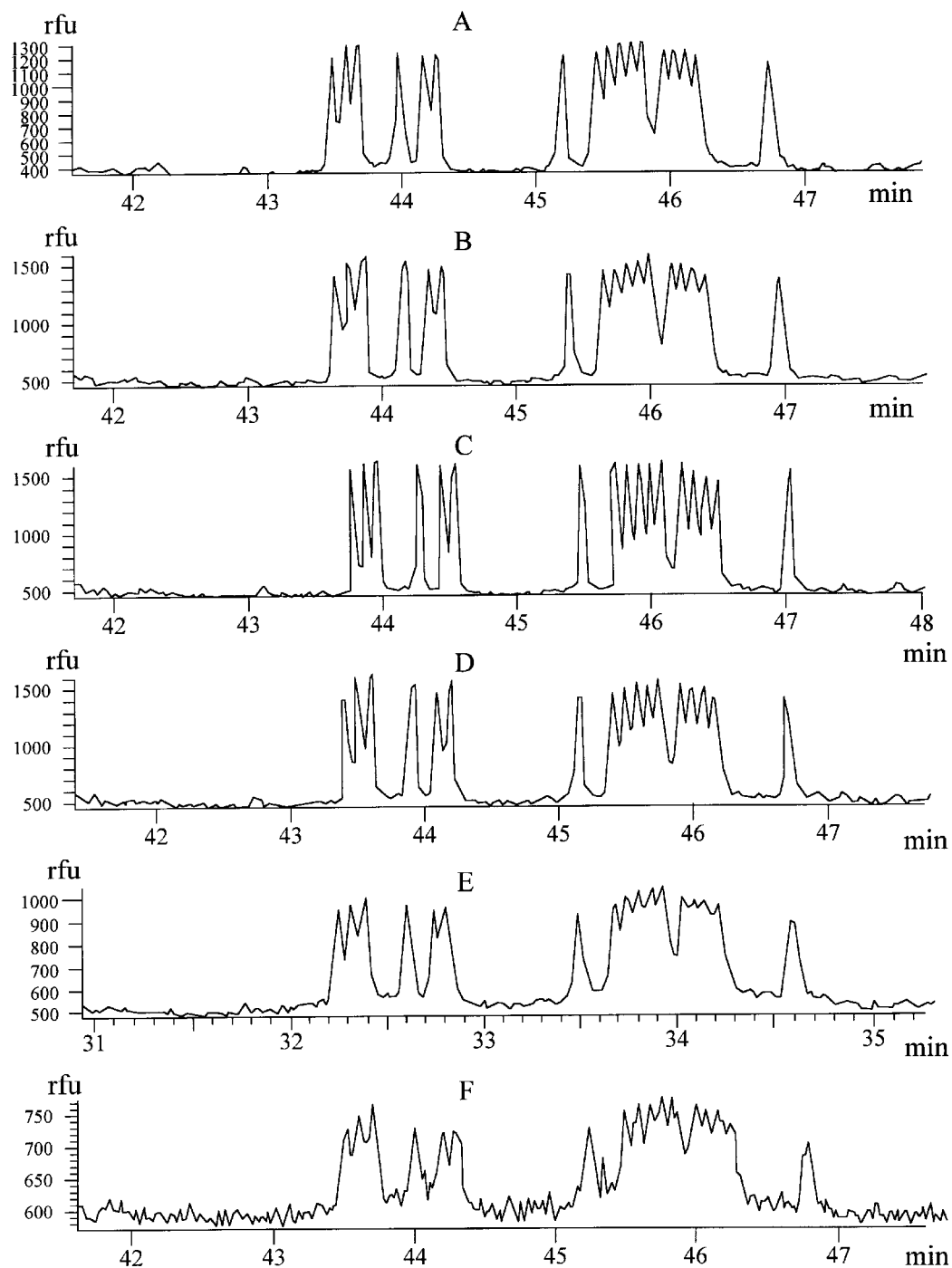

EXAMPLE 4
CZE separation of DNA sequencing fragments in poly-ADEA coated capillaries DNA sequencing ladder (T track) of M13mp18 was separated at room temperature in ADEA coated capillaries (75 μm I.D., 195 μm O.D., total length 65 cm, effective length 40 cm) assembled into an array of 16 capillaries. The separation matrix contained 2% hydroxyethyl cellulose (MW 90–105K), 6 M urea, 10% formamide and 1× TBE buffer, pH 8.1. The separation efficiency of column in separation techniques is usually expressed as the number of theoretical plates generated by a standard analyte per column length. For the case of DNA sequencing we proposed Relative Valley Depth to evaluate the separation performance of the DNA sequencing runs. The method uses T track of M13mp18 DNA which has a characteristic sequence containing a peak quintuplet followed by a peak quadruplet. Relative depth of valleys between the peak in the quadruplet is used to calculate Relative Valley Depth. For baseline separation, relative valley depth equals 100%, whereas for a poor performance, where the quadruplet is not distinguished by valleys RVD equals 0%. RVD higher than 33% is accepted as a sign of good separation performance and a good wall coating. (Poor quality of samples or sieving matrix can deteriorate separation and thus mimic poor wall coating.) Polyacrylamide wall coating hardly survives few tens of runs over one hundred. FIGS. 5A–5F show an example of separation of the characteristic sequence of M13mp18 in six polyacrylamide coated capillaries after 118 runs. In these electropherograms, the deterioration of the coating is shown by the inability of some of the capillaries to separate peaks. FIG. 5C continues to show adequate separation. However, FIGS. 5E and 5F show degradation of resolution. This loss of resolving power indicates that the capillaries must be replaced. The ADEA wall coating can efficiently separate DNA sequencing fragments, even after 500 sequencing runs. FIGS. 4A–4E show an example of separation of the characteristic sequence of M13mp18 in five ADEA coated capillaries after 500 runs. Even after 500 runs, almost 5 times the amount of runs where degradation was seen in polyacrylamide coated capillaries, resolution in the ADEA columns remain strong. RVD of the quadruplet peak remains higher than 33% for all five capillaries. This indicates that ADEA coated capillaries do not degrade even after 500 runs.

What is claimed is:

1. A capillary electrophoresis system for the separation of molecules, the system comprising:

a capillary;

a static polymeric coating on the interior of said capillary wherein the polymeric coating is comprised of polymerized monomeric subunits, wherein one of said polymerized monomeric subunits has the formula:

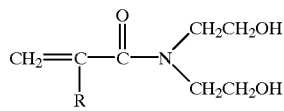

wherein R is —H or —CH$_3$;

a basic matrix filling the interior of said capillary; and electrodes in electrical communication with opposing ends of said capillary.

2. The system of claim 1, wherein said coating is comprised of a homopolymer of the compound of the formula:

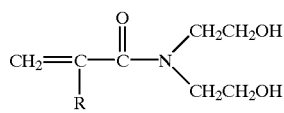

wherein R is —H or —CH$_3$.

3. The system of claim 1, wherein said coating is comprised of a copolymer wherein one component of the copolymer is a compound of the formula:

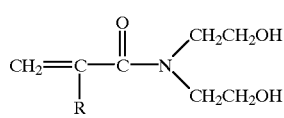

wherein R is —H or —CH$_3$.

4. The system of claim 3, wherein a second component of said copolymer is acrylamide.

5. The system of claim 3, wherein a second component of said copolymer is acryloylaminoethoxyethylglucopyranose.

6. A method to separate molecules by electrophoresis, the method comprised of the steps:

providing a capillary;

coating the capillary with a static polymeric coating, wherein the static polymeric coating is comprised of polymerized monomeric subunits, wherein one of said polymerized monomeric subunits has the formula:

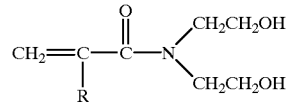

wherein R is —H or —CH$_3$;

filling the capillary with a basic separation matrix;

adding a sample to one end of said capillary;

introducing electrical current through said capillary to separate molecules.

7. The method of claim 6, the method comprised of the further steps of:

a) emptying the matrix containing sample from the capillary;

b) rinsing the capillary;

c) refilling the capillary with a basic separation matrix;

d) adding a sample to one end of said capillary;

e) introducing electrical current through said capillary to separate molecules; and f) repeating steps a–e.

8. The method of claim 7 wherein the step of repeating steps a–e occurs 500 times.

9. The method of claim 8 wherein said step of coating the capillary with a static coating is effected by:

introducing a first monomer of the formula:

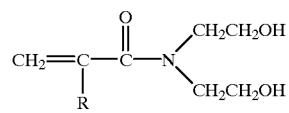

wherein R is —H or —CH$_3$
   into the capillary;

introducing a second monomer into the capillary; and inducing polymerization of said monomers through the use of an initiator means.

10. The method of claim 7 wherein said step of coating the capillary with a static coating is effected by coating the capillary with a homopolymer of the compound of the formula:

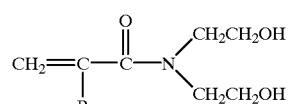

wherein R is —H or —CH$_3$.

11. The method of claim 7 wherein said step of coating the capillary with a static coating is effected by coating the capillary with a copolymer, wherein one compound of the copolymer is a compound of the formula:

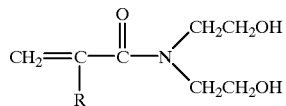

wherein R is —H or —CH₃.

12. The method of claim 11 wherein said step of coating the capillary with a static coating is effected by coating the capillary with a copolymer, wherein one compound of the copolymer is a compound of the formula:

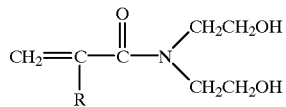

wherein R is —H or —CH₃;
and a second compound of the copolymer is acrylamide.

13. The method of claim 11 wherein said step of coating the capillary with a static coating is effected by coating the capillary with a copolymer, wherein one compound of the copolymer is a compound of the formula:

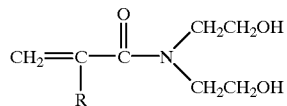

wherein R is —H or —CH₃;
and a second compound of the copolymer is acryloylaminoethoxyethylglucopyranose.

14. The method of claim 7 wherein said step of coating the capillary with a static coating is effected by:
introducing a monomer of the formula:

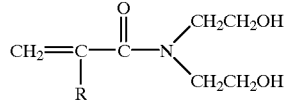

wherein R is —H or —CH₃
into the capillary; and
inducing polymerization of said monomers through the use of an initiator means.

* * * * *